(12) United States Patent
Arning et al.

(10) Patent No.: US 8,171,039 B2
(45) Date of Patent: May 1, 2012

(54) STRING PATTERN ANALYSIS

(75) Inventors: Andreas Arning, Tuebingen (DE); Roland Seiffert, Herrenberg (DE)

(73) Assignee: International Business Machines Corporation, Armonk, NY (US)

( * ) Notice: Subject to any disclaimer, the term of this patent is extended or adjusted under 35 U.S.C. 154(b) by 661 days.

(21) Appl. No.: 12/351,527

(22) Filed: Jan. 9, 2009

(65) Prior Publication Data

US 2009/0182744 A1 Jul. 16, 2009

(30) Foreign Application Priority Data

Jan. 11, 2008 (EP) .................................... 08100342

(51) Int. Cl.
*G06F 7/00* (2006.01)
*G06F 17/30* (2006.01)

(52) U.S. Cl. ......................... 707/758; 707/917

(58) Field of Classification Search .................. 707/705, 707/706, 758, 759, 769, 780, 917
See application file for complete search history.

(56) References Cited

U.S. PATENT DOCUMENTS

| | | | |
|---|---|---|---|
| 5,615,341 A | 3/1997 | Agrawal et al. | |
| 6,018,736 A * | 1/2000 | Gilai et al. | 707/6 |
| 6,338,057 B1 * | 1/2002 | Weeks | 707/736 |
| 6,466,901 B1 | 10/2002 | Loofbourrow et al. | |
| 6,741,985 B2 * | 5/2004 | Green | 707/742 |
| 2002/0048277 A1 * | 4/2002 | Bennett | 370/412 |
| 2003/0061025 A1 | 3/2003 | Abir | |
| 2009/0208955 A1 * | 8/2009 | Robins et al. | 435/6 |

FOREIGN PATENT DOCUMENTS

| | | |
|---|---|---|
| EP | 1032896 B1 | 3/2002 |
| WO | 199927469 A1 | 6/1999 |

* cited by examiner

*Primary Examiner* — Marc Somers
(74) *Attorney, Agent, or Firm* — Steven L. Nichols; Van Cott, Bagley, Cornwall & McCarthy PC

(57) ABSTRACT

A method of analyzing a string-pattern includes defining a minimum length (Lmin_1) of substrings (STR_A_B) to be considered; defining a maximum length (Lmax_1) of substrings (STR_A_B) to be considered; with a computer, searching the string-pattern for substrings (STR_A_B) with a length in an interval between the minimum length (Lmin_1) and the maximum length (Lmax_1); counting an occurrence (Occ_A_B) of each substring (STR_A_B) found with a length in the interval between the minimum length (Lmin_1) and the maximum length (Lmax_1); and pruning away a number of the substrings (STR_A_B) that meet one or more criteria. The criteria are selected from the group consisting of (1) being contained inside the maximum substring (STR_A_C) in a subset (SET_A) of substrings (STR_A_B), (2) being shorter than the maximum substring (STR_A_C), (3) occurring with a same frequency as the maximum substring (STR_A_C), and combinations thereof.

16 Claims, 7 Drawing Sheets

STRING PATTERN ANALYSIS

BACKGROUND OF THE INVENTION

The present invention relates to a string pattern analysis method and to a program product for string pattern analysis.

Providing the ability to perform searches in string patterns such as texts or biological sequence data is a commercially prosperous area. However, methods which are used, for instance, in an internet environment successfully cannot simply be transferred to enterprise environments. Additionally, content oriented issues become more and more interesting. These methods are semantic-based and less dependent on internet-specific properties. Compared to link analyses and the like, these methods are far more complex and typically language dependent.

In most of today's computer systems, text representation is not reflecting the real chunks of which the text is composed. In particular, an always co-occurring sequence of words is usually not represented as a chunk but as a distinct set of words. Knowing the real chunks in a text, i.e. long and very long substrings, however, is desirable for several reasons. It allows for a more compact representation of the text and for a better understanding of the text content, since the beginning and ending of frequent chunks are important spots in the text. In particular, elements occurring adjacently to chunks are frequently related to each other, which, for example, would allow for an automatic detection of taxonomies. For reasons of complexity, however, prior art algorithms have problems in finding the maximum substrings even in short texts since the potential number of substrings explodes with the size of the texts.

A main task in content oriented analyses usually is an adequate conceptualization, i.e. acquiring the concepts which are handled in a text as precisely as possible. Conceptualization may require finding a concept of a text in several steps (such as linguistic analysis, noun group determination, statistical relevance determination, etc.). When processing text for search or other tasks such as conceptualization (categorization) or clustering, the first step usually is to identify a basic set of terms on which higher-level components should operate. This process tries to identify meaningful parts of the overall text, often using immediate context that can be considered as "concepts" or at least "concept candidates."

In most cases concepts are represented as noun groups in a language. In order to find noun groups in text, a syntactic analysis, which is language dependent and computationally expensive, may be required.

In most cases and across languages, noun groups are formed by consecutive elements of the text. In English, for example, noun groups are usually presented as a sequence of adjectives followed by a sequence of nouns. In German noun groups are usually presented as a sequence of adjectives followed by a single (but potentially compound) noun. Not all noun groups should be truly considered as "concepts," but only as "candidates." Usually, some part of the noun group constitutes the concept (i.e. a class of objects) and the rest of the associated words function to identify a particular object or instance of the concept. Therefore, identifying noun groups is not enough to get to a concept level. Some type of contextual analysis is needed. Besides requiring enormous computing power, such analyses are often language dependent.

However, even in applications such as genome analysis, although only few letters are used as an "alphabet" to represent the essential components, time and space consuming scaling problems appear.

In the paper of Stefan Kurz & Chris Schleiermacher, *REPuter: Fast Computation of Maximal Repeats in Complete Genomes,* 15 BIOINFORMATICS 426, (1999), a software tool is implemented that computes exact repeats and palindromes in entire genomes. Deoxyribonucleic acid (DNA) is a long polymer made from repeating units called nucleotides, wherein the DNA double helix is held together by hydrogen bonds between four bases attached to the two strands. The four bases found in DNA are adenine (A), cytosine (C), guanine (G), and thymine (T). These four bases are attached to the sugar/phosphate in the strands to form the complete nucleotide. Although genomes in DNA can be represented by an alphabet of only four characters, i.e. capital letters A, C, G, T, this reveals inherent scaling problems in the analysis. For instance, 160 MB of storage space is needed for 11 MB doing the genome analysis. For the handling of 63 characters, however, with 26 capital letters, 26 lower case letters, 10 numbers (0-9), 1 whitespace or even 256 characters for ASCII, the suffix tree in the memory grows dramatically.

BRIEF SUMMARY OF THE INVENTION

According to one embodiment of the present invention, a method of analyzing a string-pattern is disclosed, comprising defining a threshold for a minimum number of occurrences of a number of substrings (STR_A_B) contained in the string-pattern, defining a minimum length (Lmin_1) of substrings (STR_A_B) to be considered, defining a maximum length (Lmax_1) of substrings (STR_A_B) to be considered, searching the string-pattern for substrings (STR_A_B) with a length in an interval between the minimum length (Lmin_1) and the maximum length (Lmax_1), counting an occurrence (Occ_A_B) of each substring (STR_A_B) found with lengths in the interval between the minimum length (Lmin_1) and the maximum length (Lmax_1), and pruning away a number of the substrings (STR_A_B) that meets a number of criteria, wherein the criteria are selected from the group consisting of being contained inside the substring (STR_A_C) in a subset (SET_A) of substrings (STR_A_B), being shorter than the substring (STR_A_C), occurring with the same frequency as the substring (STR_A_C), and combinations thereof.

According to another embodiment of the present invention, a data processing system is disclosed comprising a number of processors, a number of memory devices coupled to the processors, and a display configured to display data to the user based on instructions from the processor, wherein the processors are configured to define a threshold for a minimum number of occurrences of a number of substrings (STR_A_B) contained in a string-pattern, define a minimum length (Lmin_1) of the substrings (STR_A_B) to be considered, define a maximum length (Lmax_1) of the substrings (STR_A_B) to be considered, search the string-pattern for substrings (STR_A_B) with a length in an interval between the minimum length (Lmin_1) and the maximum length (Lmax_1), count an occurrence Occ_A_B of each substring (STR_A_B) found with lengths in the interval between the minimum length (Lmin_1) and the maximum length (Lmax_1), pruning away a number of the substrings (STR_A_B) that meets a number of criteria, wherein the criteria are selected from the group consisting of being contained inside the substring (STR_A_C) in a subset (SET_A) of substrings (STR_A_B), being shorter than the substring (STR_A_C), occurring with the same frequency as the substring (STR_A_C), and combinations thereof, and display the maximum substrings (STR_A_C) to the user on the display.

According to another embodiment of the present invention, a computer program product for analyzing a number of string-patterns is disclosed, the computer program product comprising a computer usable medium having computer usable program code embodied therewith, the computer usable program code comprising computer usable program code configured to define a threshold for a minimum number of occurrences of a number of substrings (STR_A_B) contained in the string-pattern, computer usable program code configured to define a minimum length (Lmin_1) of substrings (STR_A_B) to be considered, computer usable program code configured to define a maximum length (Lmax_1) of substrings (STR_A_B) to be considered, computer usable program code configured to search the string-pattern for substrings (STR_A_B) with a length in an interval between the minimum length (Lmin_1) and the maximum length (Lmax_1), computer usable program code configured to count an occurrence Occ_A_B of each substring (STR_A_B) found with lengths in the interval between the minimum length (Lmin_1) and the maximum length (Lmax_1), computer usable program code configured to prune away a number of the substrings (STR_A_B) that meets a number of criteria, wherein the criteria are selected from the group consisting of being contained inside the substring (STR_A_C) in a subset (SET_A) of substrings (STR_A_B), being shorter than the substring (STR_A_C), occurring with the same frequency as the substring (STR_A_C), and combinations thereof, and computer usable program code configured to presenting maximum substrings (STR_A_C) to a user.

According to another embodiment of the present invention, a method of analyzing a number of string-patterns is disclosed, comprising defining a subset (SET_A) of substrings (STR_A_B) in the string-pattern, monitoring all the substrings (STR_A_B) and their occurrence counts (Occ_A_B) in the subset (SET_A) of substrings (STR_A_B), pruning away each substring (STR_A_B) if the substring (STR_A_B) is subsumed by a longer substring (STR_A_C) in the subset (SET_A) of substrings (STR_A_B) with the same occurrence count (Occ_A_C), and presenting maximum substrings (STR_A_C) to a user.

DETAILED DESCRIPTION OF THE INVENTION

Figure 1:
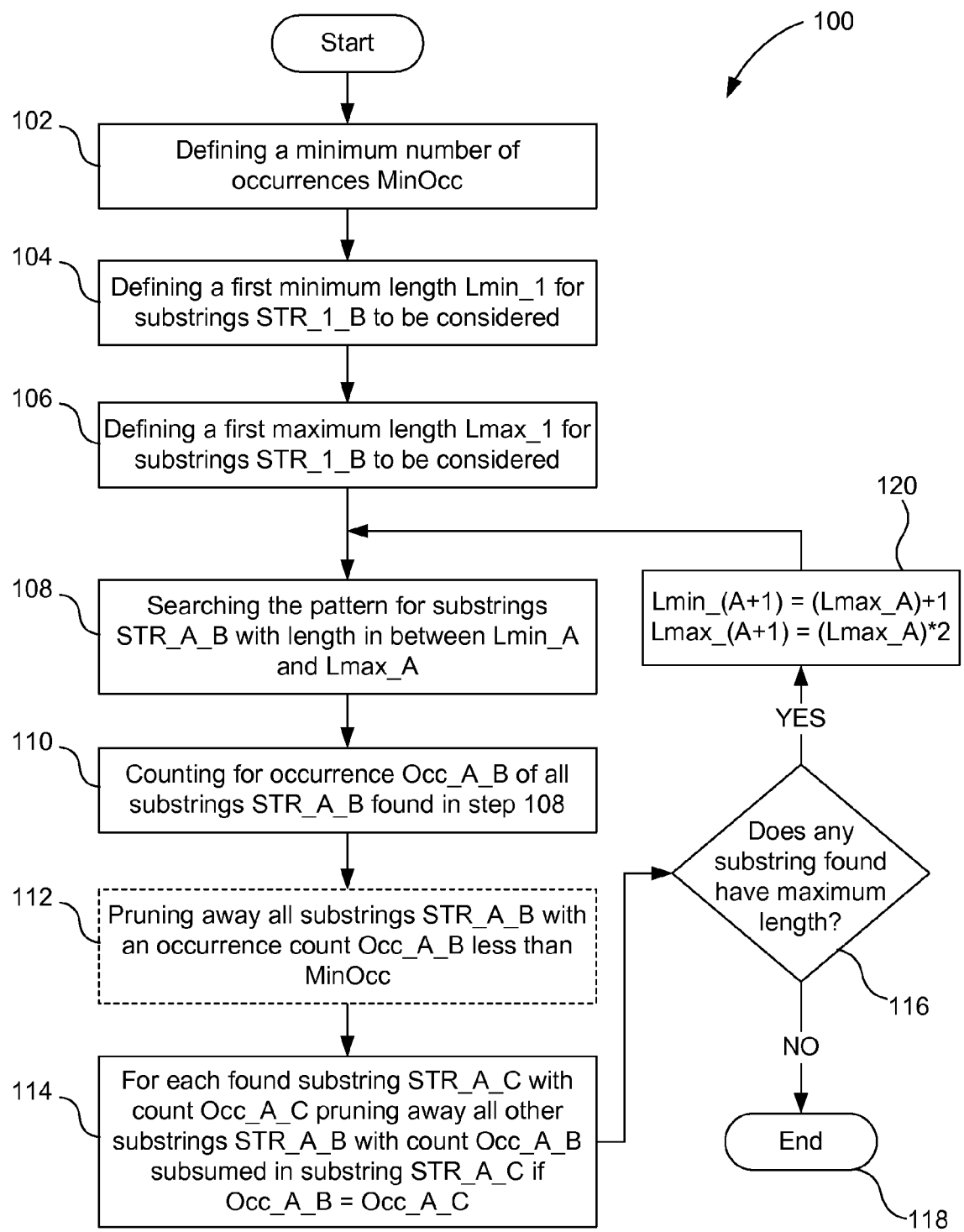
FIG. 1 is a flow chart illustrating a string pattern analysis method according to an embodiment of the present exemplary system and method.

As will be appreciated by one skilled in the art, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including, but not limited to the Internet, wireline, optical fiber cable, RF, etc.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

It is an object of the present invention to provide an efficient string pattern analysis method, particularly for finding maximal substrings, and a program product for string pattern analysis. A string pattern analysis method, and, particularly, a pattern of words or a bioinformatics pattern, is proposed. The method may comprise the steps of iteratively defining a subset of substrings in the pattern, keeping track of all the substrings in the subset of substrings, and pruning away each substring that is subsumed by a longer substring in the subset of substrings with same occurrence count. Favorably, the method allows finding maximal substrings in the string pattern. The efficiency is improved resulting in a better scalability of systems which are used to perform the preferred method. These systems are cheaper and faster.

The proposed method may be used for analyzing mass data such as from bioinformatics, genome analysis, real time data of satellites, and the like. The method may be used for content management and search engines, for instance. The method is space and time efficient, because it is not necessary to keep track of the complete set of substrings at once. Instead, the method keeps track of only a subset of substrings and prunes away such substrings which are subsumed in other substrings. For instance, a subsumed substring may be a smaller substring than is often co-occurring with the same leading or trailing neighbor and/or may be contained inside the substring and/or may be occurring with the same frequency of occurrence as the substring. This pruning step reduces the complexity in a real occurring string pattern, e.g. a text. Typically in algorithms known in the art the string pattern, e.g. the text, has to be stored in full length and usually several times the fill length. This results in high computing power needed and high storage consumption. Other than this, the proposed method is much more efficient in computing power and storage consumption. One application of the proposed method may be conceptualization of a text.

According to another aspect of the invention, a program product is proposed, comprising a computer useable medium including a computer readable program, wherein the computer readable program, when executed on a computer, causes the computer to iteratively define a subset of substrings in the pattern, keep track of the subset of substrings, and prune away each substring that is subsumed by a longer substring in the subset with the same occurrence count.

A string pattern analyzing method may comprise the steps of defining a subset of substrings in the pattern, keeping track of all the substrings in the subset of substrings, and pruning away each substring that is subsumed by a longer substring in the subset of substrings with the same occurrence count. The invention is exemplified for text as a string pattern. It is to be understood, however, that the invention is not restricted to text but can be applied to any string pattern such as in genome analysis and the like.

An embodiment of the method is depicted in FIG. 1 generally as flow chart (100) wherein a string pattern is analyzed to find substrings STR_A_B contained in the pattern. "A" is an index indicating the actual number of the iteration "A," with a running between 1 and "D," wherein "D" denotes a total number of iterations "A." "B" is a parameter denoting individual substrings in the iteration step "A."

In a first step (step 102), a threshold for a minimum number of occurrences (MinOcc) of a substring STR_A_B is defined, and substrings STR_A_B below the threshold MinOcc are ignored. In one embodiment, the number of minimum occurrence may defined as MinOcc=2. Typically, the threshold for MinOcc is kept constant for all iterations "A." However, the minimum occurrence MinOcc may be increased if necessary. Due to the threshold, the full and complete text may not be considered as one substring STR_A_B. Therefore, substrings STR_A_B are always subsets SET_A of the full text.

In steps 104 and 106, a first minimum length Lmin_1 and a first maximum length Lmax_1 of substrings STR_1_B to be considered in a first iteration step with A=1 looping over the text, may be defined. In one exemplary embodiment, the first values may be Lmin_1=1 and Lmax_1=5.

In step 108, the pattern may then be searched for substrings STR_1_B with a length in an interval between the minimum length Lmin_1 and the maximum length Lmax_1. In step 110, the occurrence Occ_A_B of each substring STR_A_B found with lengths in the interval between Lmin_1 and Lmax_1 may be counted. In optional step 112, all substrings STR_A_B with an occurrence count Occ_A_B less than the minimum occurrence threshold MinOcc may be pruned away.

For each iteration "A," a subset of substrings SET_A may be defined in the pattern. SET_A of substrings STR_A_B may be different for each iteration "A." All the substrings STR_A_B and the occurrence counts Occ_A_B in the subset SET_A of substrings (SET_A) may be maintained and/or recorded.

In step 114, all other sub-substrings, STR_A_B, that are at least one of the following, may be pruned away for each found substring STR_A_C: (1) being contained inside the substring STR_A_C in the subset SET_A of substrings STR_A_B, (2) being shorter than the substring STR_A_C, and (3) occurring with the same frequency as the substring STR_A_C, i.e. with same occurrence count Occ_A_C. In one embodiment, all three conditions may be required to be fulfilled for substrings STR_A_B to be pruned away. Due to step 114, the amount of substrings STR_A_B to be stored and analyzed may be dramatically reduced to the number of maximum substrings STR_A_C. The index "C" may denote the maximum substring.

At step 116, it is determined if any substring found has the maximum length. If none of the substrings STR_A_B found has the maximum length Lmax_A (NO, step 116), then the process terminates at step 118. If, however, at least one substring STR_A_B has a length of Lmax_A (YES, step 116), new minimum and maximum lengths may be defined at step 120, and steps 108 through 116 may be repeated in the next iteration loop with A=A+1. In one embodiment, the iteration "A" can stop, for instance, if a maximum number "D" of iterations "A" or a predefined maximum length Lmax_A is exceeded. In one embodiment, the substrings STR_A_C found may be stored in a TRIE structure or any other suitable ordered tree data structure. Step 120 may define a new minimum and maximum length variables with the new minimum length set to Lmin_(A+1)=(Lmax_A)+1 and the new maximum length set to Lmax_(A+1)=(Lmax_A)*2.

One exemplary method may be independent of language when applied to a text. Therefore, this exemplary method may enable advanced text functions when applied to a text. By way of example, when all maximal substrings STR_A_C in a text are found with the exemplary method, all maximal substrings STR_A_C may be used as an approximate substitute for concepts of the text. This may be improved when statistical relevance of the maximal substrings STR_A_C found is included. An additional preprocessing step prior to identifying maximal substrings STR_A_C may be performed, and thus linguistic variants of words contained in the substrings may be eliminated. This may result in an improvement of the quality of the substrings found. Additionally or alternatively, it may be possible to reduce inflected forms of words in the pattern to their morphological stems. This is still cost efficient as no sophisticated complex linguistic analysis is necessary. The substring STR_A_C found may be presented to a user, and in one embodiment, together with its count. Further, when determining sub-substrings STR_A_B of each of the identified maximal substrings STR_A_C, a statistical filter may be applied to avoid "overfitting." Such sub-substrings STR_A_B may be considered in a statistical and/or a linguistic based selection procedure. For example, if a maximal substring in a text is "ABC CORPORATION HAS," the verb "HAS" may be omitted.

A further quality improvement may be achieved if the method blinds out the highest detail level and goes back to a lower detail level if a frequency of one or more maximal substrings STR_A_B found in the text drops below a defined threshold, e.g. if the maximal substring STR_A_C found become very rare. This threshold may be chosen dependent on the complexity of the text or the like. The example elucidated above is one possible and exemplary usage of the method to identify maximal substrings STR_A_C in a text.

The invention can take the form of an entirely hardware embodiment, an entirely software embodiment, or an embodiment containing both hardware and software elements. In an exemplary embodiment, the invention may be implemented in software, which includes but is not limited to firmware, resident software, microcode, etc.

Furthermore, the invention may take the form of a computer program product accessible from a computer-usable or computer readable medium providing program code for use by or in connection with a computer or any instruction execution system. For the purposes of this description, a computer-usable or computer readable medium may be any apparatus that can contain, store, communicate, propagate, or transport the program for use by or in connection with the instruction execution system, apparatus, or device.

The medium may be an electronic, magnetic, optical, electromagnetic, infrared, or semiconductor system (or apparatus or device) or a propagation medium. Examples of a computer-readable medium may include a semiconductor or solid state memory, magnetic tape, a removable computer diskette, a random access memory (RAM), a read-only memory (ROM), a rigid magnetic disk, and an optical disk. Current examples of optical disks include compact disk-read-only memory (CD-ROM), compact disk-read/write (CD-R/W) and DVD.

Figure 2:
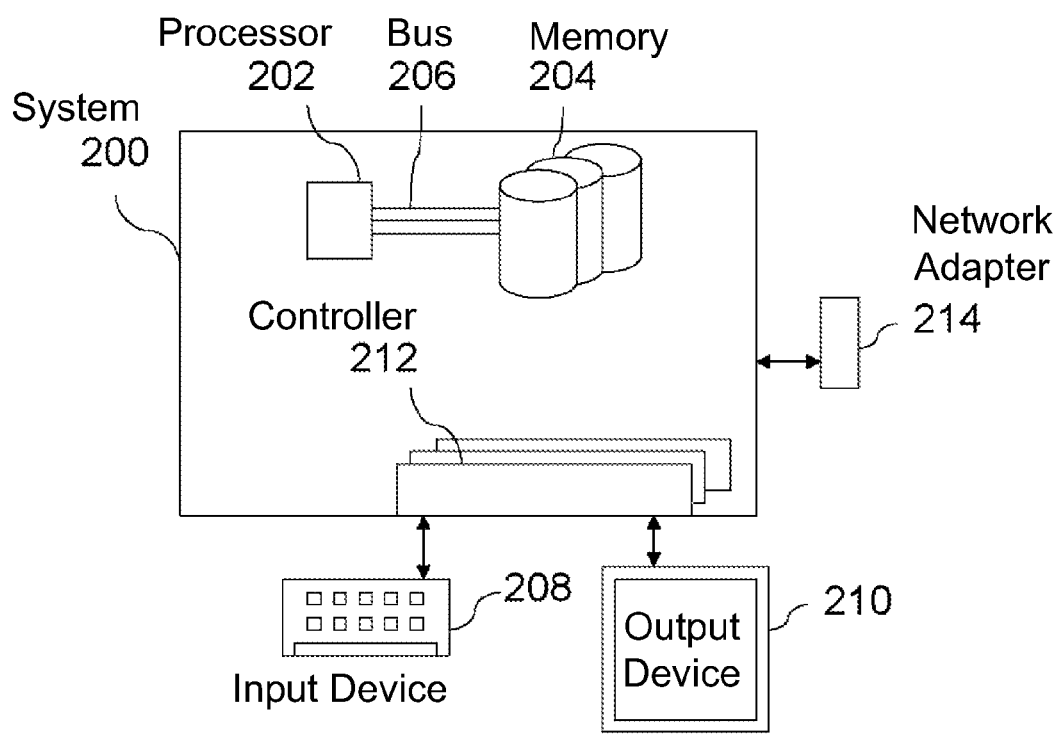
FIG. 2 is a data processing system for performing the method of FIG. 1 according to an embodiment of the present exemplary system and method.

FIG. 2 illustrates an exemplary data processing system (200) (computer) suitable for storing and/or executing program code may include at least one processor (202) coupled directly or indirectly to memory elements (204) through a system bus (206). The memory elements (204) may include local memory employed during actual execution of the program code, bulk storage, and cache memories which may provide temporary storage of at least some program code in order to reduce the number of times code must be retrieved from bulk storage during execution.

Input/output or I/O-devices (208, 210) (including, but not limited to keyboards, displays, pointing devices, etc.) may be coupled to the data processing system (200) either directly or through intervening I/O controllers (212). Network adapters (214) may also be coupled to the system (200) to enable the data processing system or remote printers or storage devices through intervening private or public networks. Modems, cable modem, and Ethernet cards are just a few of the currently available types of network adapters.

Figure 3A:
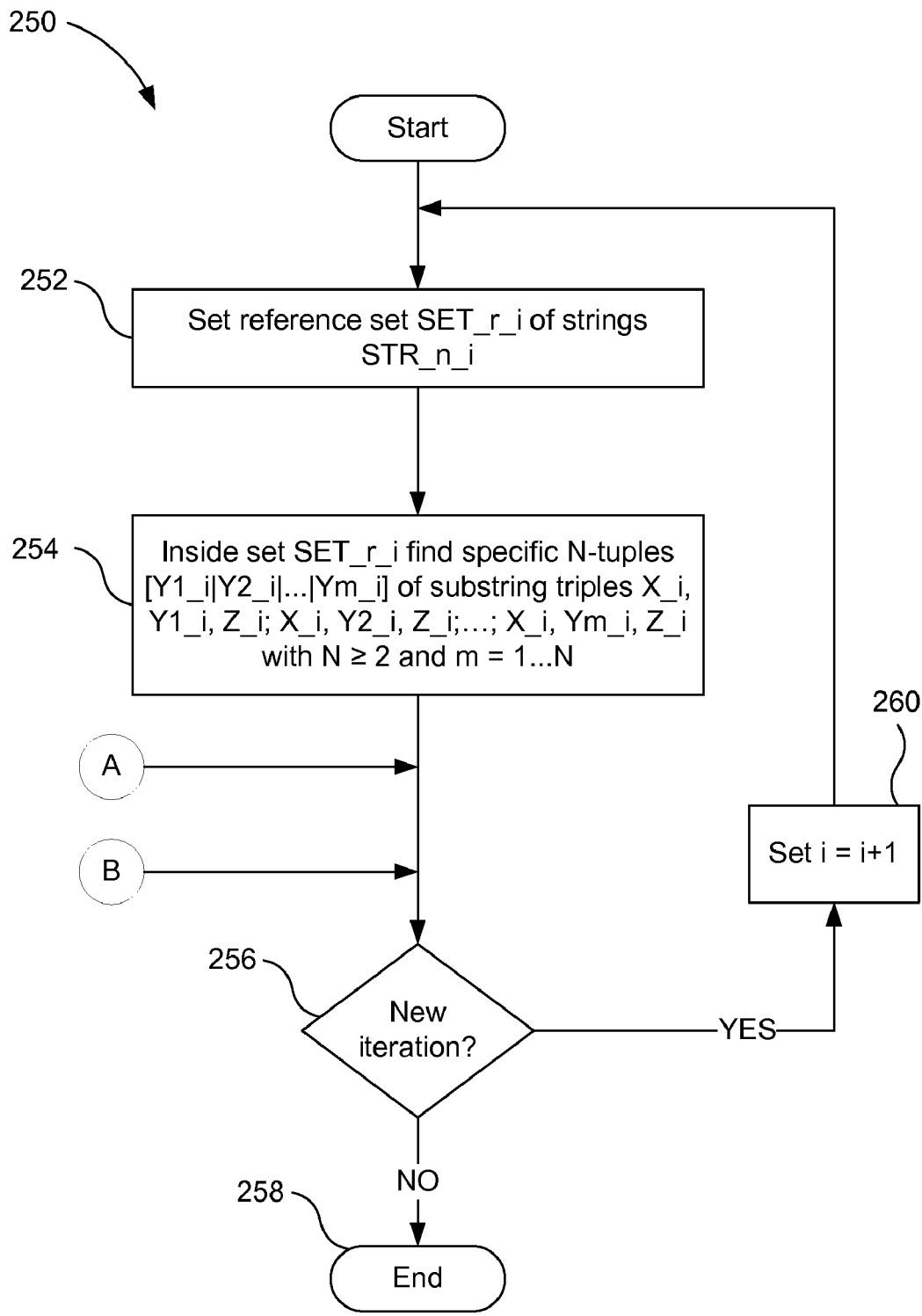
FIGS. 3A and 3B comprise a flow chart of a first conceptualization method for a string pattern according to an embodiment of the present exemplary system and method.

FIG. 3A illustrates another exemplary aspect of the present invention which considers a string-pattern-conceptualization method as depicted in flowchart (250). By way of example, maximal substrings found in a method, as elucidated above may be applied in such a conceptualization method. In one embodiment, the conceptualization method, however, may not be restricted to the use of maximal substrings. Instead, any set of substrings of a string pattern may be used. The goal may be to compute a set SN of N-tuples of strings. In the following, these N-tuples of strings are called "N-siblings." It may be necessary to find the maximum set i.e. all N-siblings for $N \geq 2$. In one exemplary embodiment, ranking the set SN and pruning the set SN to the set most relevant to a given scenario may also be performed.

In one embodiment, the string pattern may be a text. The method provides an approximate conceptualization by detecting related concepts from a given amount of text, e.g. in a search engine. This exemplary method is time and resource efficient, particularly when combined with the above exemplary string pattern analysis method to find maximal substrings in a string pattern. In order to avoid unnecessary repetitions, reference is made to the preceding description of the string pattern analysis method if such an analysis method should be combined with this exemplary conceptualization method.

In one embodiment, a string concatenation operator $\otimes$ may first be defined. $X \otimes Y$ means that the strings X and Y are concatenated. $(X \otimes Y) \otimes Z$ is equivalent to $X \otimes (Y \otimes Z)$ and is abbreviated to $X \otimes Y \otimes Z$.

Let R be a set of strings ("reference set"), let U be the universe of all strings, let X, Y1, Y2, ..., YN, Z be elements of U, and let e be the empty string. Then SN, the set of "N-siblings," may be defined as follows:

$$SN = \{(Y1, \ldots, YN) \mid \underset{1 \leq i \leq N}{\forall} Yi \neq e \wedge \underset{i \neq j}{\forall} Yi \neq Yj \wedge \exists X \in U,$$
$$Z \in U : (\underset{1 \leq i \leq N}{\forall} X \otimes Yi \otimes Z \in R \wedge (X \neq e \vee Z \neq e))\}$$

In one case of the present exemplary system and method, index N=2. In this case, "2-siblings," i.e. pairs of substrings are searched.

$$S2 = \{(Y1, Y2) \mid Y1 \neq e \wedge Y2 \neq e \wedge Y1 \neq Y2 \wedge \exists X \in U,$$
$$Z \in U : (X \otimes Y1 \otimes Z \in R \wedge X \otimes Y2 \otimes Z \in R \wedge (X \neq e \vee Z \neq e))\}$$

This means that siblings Y1 and Y2, which are different from each other, are searched and both occur in the set of strings R as concatenations of identical prefixes X and suffixes Z, where at least the prefix X or the suffix Z is non-empty. The reference set R is denoted as SET_r_i in the following text, but R is used instead of SET_r_i for the above-mentioned formulas for compactness of the formulas.

By way of example, assume that the set SET_r_i of strings consists of the following two strings:

1. "If the process is a long-running business process then the output is . . . ."
2. "If the process is a microflow then the output is . . . ."

Here, the set of 2-siblings contains the two substrings Y1 and Y2 with:

Y1="long-running business process"
Y2="micro flow"

because there exists a prefix X

X="If the process is a "

and there exists a suffix Z

Z="then the output is"

which do satisfy all required constraints above.

In a more general case, this method may allow the empty string to be one of the siblings. Semantically, this may mean that the concepts of a set of siblings, of which one sibling is the empty string, represent optional concepts that may or may not occur in a particular context.

In this more general case, the formula simplifies to:

$$SN = \{(Y1, \ldots, YN) \mid \bigvee_{i \neq j} Yi \neq Yj \wedge \exists X \in U,$$

$$Z \in U : (\bigvee_{1 \leq i \leq N} X \otimes Yi \otimes Z \in R \wedge (X \neq e \vee Z \neq e))\}$$

and the associated formula for N=2 simplifies to:

$$S2 = \{(Y1, Y2) \mid Y1 \neq Y2 \wedge \exists x \in U,$$

$$Z \in U : (X \otimes Y1 \otimes Z \in R \wedge X \otimes Y2 \otimes Z \in R \wedge (X \neq e \vee Z \neq e))\}$$

FIG. 3A depicts a flow chart (250) representing an exemplary string pattern conceptualization method, particularly for a pattern of words. This exemplary method represents a general case and comprises the steps which are done one or "i" more times of setting a reference set SET_r_i (in the example above denoted as R) of strings STR_n_i in step 252. The reference set SET_r_i may or may not, by way of example, consist of maximal substrings. The strings STR_n_i may overlap each other. Inside the reference set SET_r_i, a search may be performed in step 254 for finding specific N-tuples of substring triples X_i,Y1_i,Z_i; X_i,Y2_i, Z_i; . . . ; X_i,Ym_i,Z_i with N≧2 and m=1 . . . N.

In step 254 each N-tuple ([Y1_i|Y2_i| . . . |Ym_i]) is considered as a candidate for representing related concepts, wherein each concatenation X_i⊗Y1_i⊗Z_i; X_i⊗Y2_i⊗ Z_i; . . . ; X_i⊗Ym_i⊗Z_i of the substrings triples X_i,Y1_i, Z_i; X_i,Y2_i,Z_i; . . . ; X_i,Ym_i,Z_i is an explicit member of the reference set SET_r_i. Each middle substring out of Y1_i, Y2_i, . . . , Ym_i is unequal to another middle substring out of Y1_i, Y2_i, . . . , Ym_i within the substring triples X_i,Y1_i,Z_i; X_i,Y2_i,Z_i; . . . ; X_i,Ym_i,Z_i found inside the reference set SET_r_i. Each prefix substring X_i is equal to all other prefix substrings X_i within the substring triples X_i,Y1_i,Z_i; X_i,Y2_i,Z_i; . . . ; X_i,Ym_i,Z_i found inside the reference set SET_r_i. Each suffix substring Z_i is equal to all other prefix substrings Z_i within the substring triples X_i,Y1_i,Z_i; X_i,Y2_i,Z_i; . . . ; X_i,Ym_i,Z_i found inside the reference set SET_r_i, and either prefix X_i or suffix Z_i is not empty.

In step 256 it is checked if a new iteration has to be done. If a new iteration has been done (YES, step 256), the iteration index is increased by one at step 260, and the loop starts again at step 252. If no new iteration has been done (NO, step 256), then the process terminates at step 258.

Figure 3B:
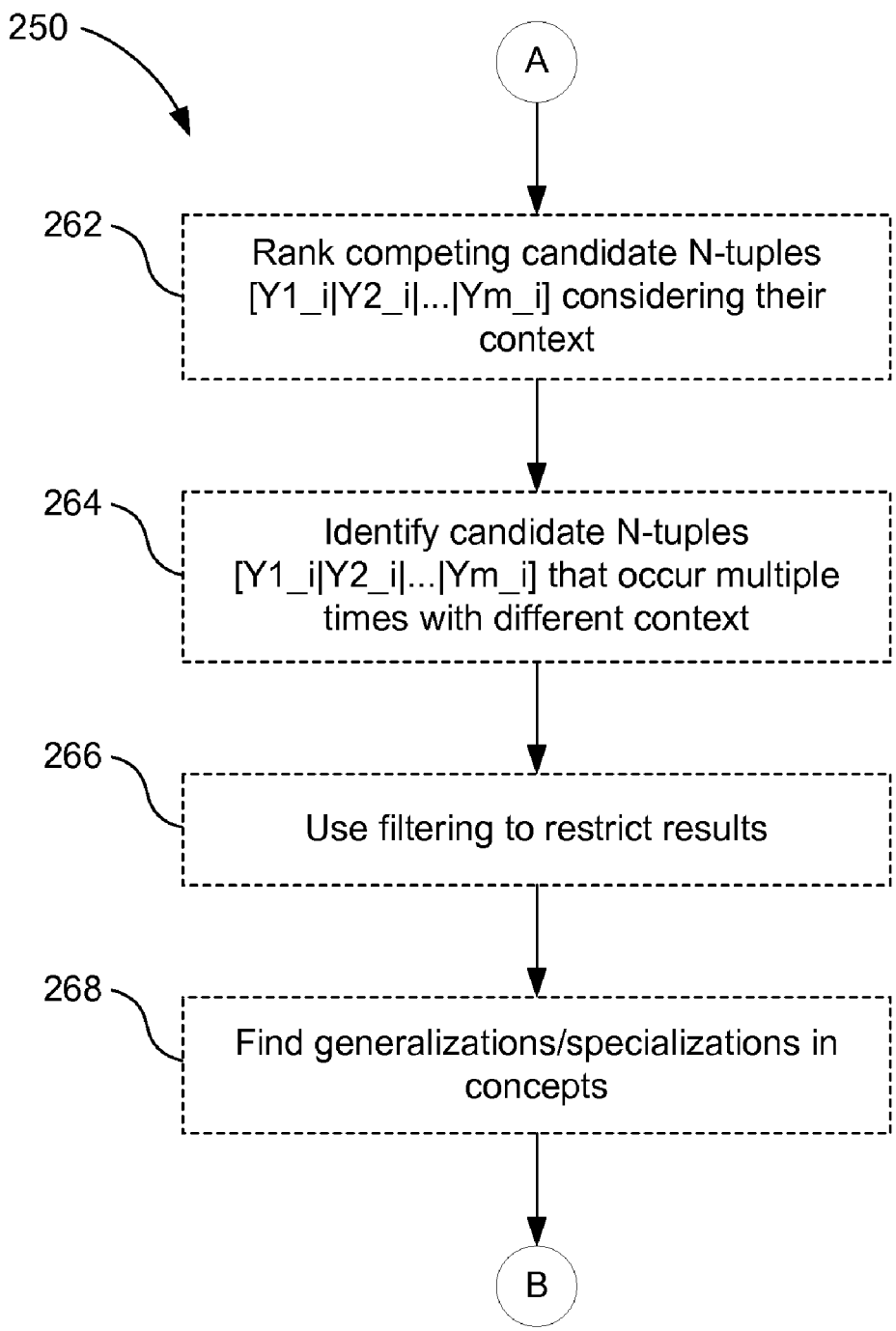

FIG. 3B illustrates optional steps between steps 256 and 258 of flow chart 250 which may be performed individually or in combination with any of the steps of FIG. 3A. In step 262, competing candidate N-tuples [Y1_i|Y2_i| . . . |Ym_i] may be ranked considering their context. For ranking it is favourable to denote each string STR_n_i with its occurrence count OCC_n_i and rank according to the occurrence. An example for this is given below with reference to FIG. 4A.

In step 264, candidate N-tuples [Y1_i|Y2_i| . . . |Ym_i] may be identified that occur multiple times with different context. In step 266, filtering may be used to restrict results. In step 268, generalizations/specializations may be found in concepts.

Figure 4A:
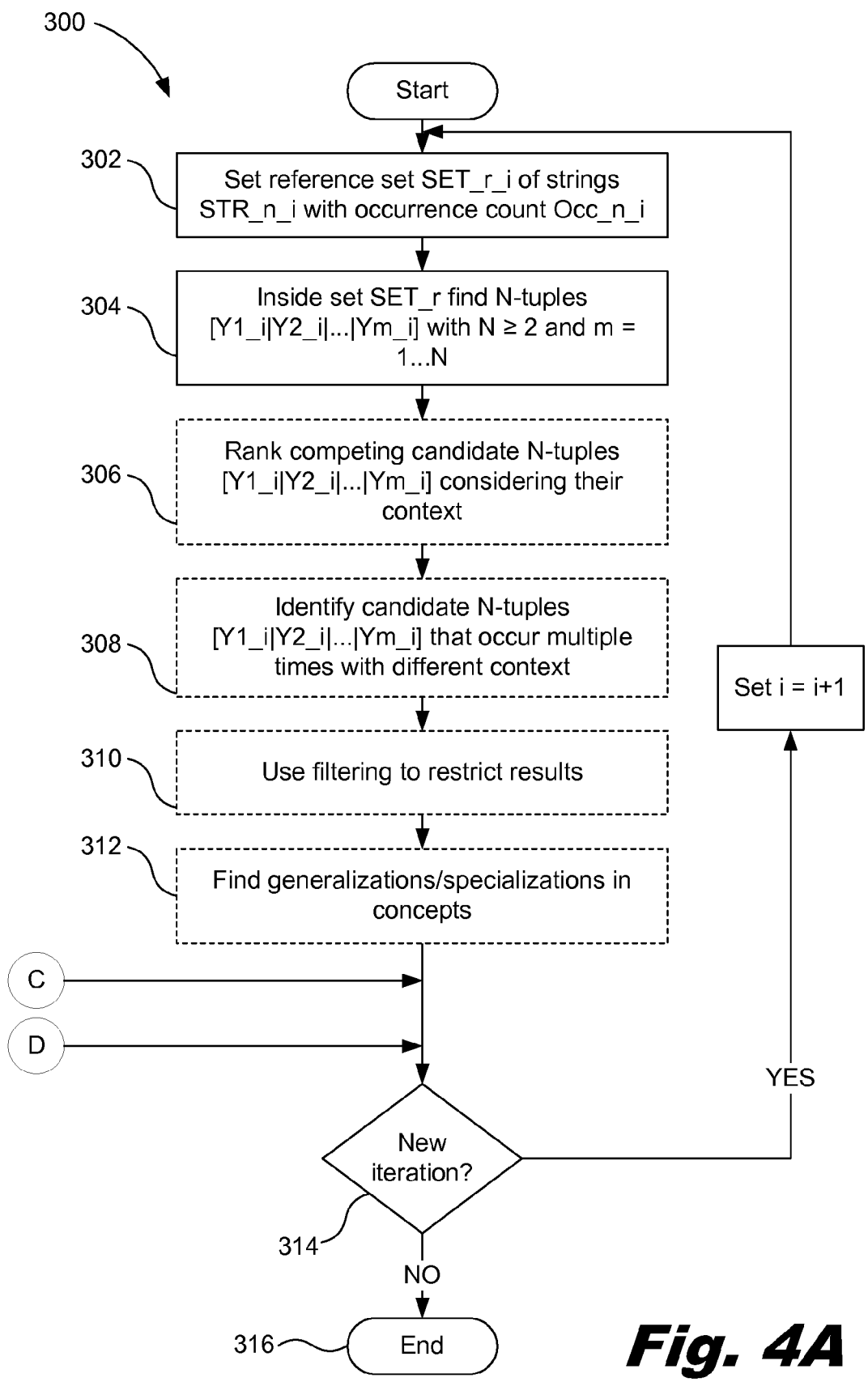
FIGS. 4A and 4B comprise a flow chart of a second conceptualization method for a string pattern for N-tuples with N=2 according to an embodiment of the present exemplary system and method.

FIG. 4A depicts a flow chart (300) representing another exemplary embodiment of the string pattern conceptualization method, particularly for a pattern of words. The preferred embodiment may comprise steps which are done one or "i" more times of (1) setting a reference set SET_r_i of strings STR_n_i, and (2) denoting each string STR_n_i with its occurrence count OCC_n_i in step 302. The reference set SET_r_i may, by way of example, consist of maximal substrings. The strings STR_n_i may overlap each other. Inside the reference set SET_r_i, a search may be performed in step 304 for finding specific N-tuples of substring triples X_i, Y1_i,Z_i; X_i,Y2_i,Z_i; . . . ; X_i,Ym_i,Z_i with N≧2 and m=1 . . . N. Each N-tuple [Y1_i|Y2_i| . . . |Ym_i] may be considered as a candidate for representing related concepts.

With N=2 the N-tuple is a pair [Y1|Y2] of substring triples X_i,Y1_i, Z_i and X_i,Y2_i,Z_i. With N=3 the N-tuple is a triple [Y1|Y2|Y3] of substring triples X_i,Y1_i,Z_i; X_i, Y2_i,Z_i; X_i,Y3_i,Z_i, etc. For each iteration "i," the reference set SET_r_i reasonably is a different set of strings STR_n_i. By way of example, the method may be done either by running the algorithm for pairs and then doing post-processing of the results by creating groups from pairs or it may be done directly from the algorithm.

As already expressed as relational formula above, the N-tuples [Y1_i|Y2_i| . . . |Ym_i] inside the SET_r_i may fulfill the following constraints. Constraint 1: Each concatenation X_i⊗Y1_i⊗Z_i; X_i⊗Y2_i⊗i Z_i; . . . ; X_i⊗ Ym_i⊗Z_i of the substring triples X_i,Y1_i,Z_i; X_i,Y2_i, Z_i; . . . ; X_i,Ym_i,Z_i is an explicit member of the reference set SET_r_i. The middle substrings Y1, Y2, . . . , Ym may, but do not have to, be explicit members. Further, the prefix substrings X_i and the suffix substrings Z_i may, but do not have to, be explicit members.

Constraint 2: Each middle substring Y1_i, Y2_i, . . . , Ym_i is unequal to another middle substring Y1_i, Y2_i, . . . , Ym_i within the substring triples X_i,Y1_i,Z_i; X_i,Y2_i, Z_i; . . . ; X_i,Ym_i,Z_i found inside the reference set SET_r_i. Constraint 3: All prefix substrings X_i within the substring triples X_i,Y1_i,Z_i; X_i,Y2_i,Z_i; . . . ; X_i,Ym_i,Z_i found inside the reference set SET_r_i are identical. Constraint 4: All suffix substrings Z_i within the substring triples X_i,Y1_i,Z_i; X_i,Y2_i,Z_i; . . . ; X_i,Ym_i,Z_i found inside the reference set SET_r_i are identical. Constraint 5: Either prefix X_i or suffix Z_i is not empty. N-tuples [Y1_i|Y2_i| . . . |Ym_i] which fulfill these constraints may be considered as candidates for being related concepts in the conceptualization algorithm.

In a first optional step 306, refinements of the base algorithm described in steps 302 and 304, may be made by ranking competing candidates according to specific criteria. In a first refinement, a ranking of competing candidate N-tuples [Y1_i|Y2_i| . . . |Ym_i] considering their context may be performed. The context is to be understood as the prefix and/or suffix string $X\_i$, $Z\_i$ accompanying the middle substrings $Y1\_1, Y2\_i, \ldots, Ym\_i$. A frequent prefix and/or suffix string $X\_i$, $Z\_i$ may be weighted lower than a less frequent prefix and/or suffix string $X\_i$, $Z\_i$.

For ranking, one or more of the following criteria (1), (2), (3) may be used. Criteria (1) and (2) are provided in optional step 306. More specifically, criteria (1) may be as follows: (1) Let occurrence sum Occ_sum_i be the sum of all occurrences of the strings $X\_i \otimes Y1\_i \otimes Z\_i; \ldots; X\_i \otimes Ym\_i \otimes Z\_i$. Let occurrence Occ_x_i be the occurrence of prefix string $X\_i$. Make sure that both values $X\_i$ and occ_sum_i are >0. Then, build a rank Rank_i as the quotient Rank_i=Occ_sum_i*Square(Occ_sum_i/Occ_x_i). Rank candidates with the highest rank Rank_i representing the most significant result.

Further, criteria (2) may be as follows: (2) Let occurrence sum Occ_sum_i be the sum of all occurrences of the strings $X\_i \otimes Y1\_i \otimes Z\_i; \ldots; X\_i \otimes Ym\_i \otimes Z\_i$. Let occurrence Occ_z_i be the occurrence of suffix string $Z\_i$. Make sure that both values $Z\_i$ and Occ_sum_i are greater than (>)0. Then, build a rank Rank_i as the quotient Rank_i=Occ_sum_i*Square(Occ_sum_i/Occ_z_i). Rank candidates with the highest rank Rank_i representing the most significant result.

The formulas used in the criteria (1) and (2) do factor in as squared term the affinity between $X\_i$, $Z\_i$, and the middle substrings. If these prefixes and suffixes co-occur almost exclusively with the found middle strings, this deserves a high rank. In addition, the formulas factor is as linear term the frequencies of the complete concatenations. If this number is significantly high, this deserves a high rank.

By way of example, frequent substrings like "the . . . and" with X=the, and Z=and may be eliminated by criteria (1) and (2). Here are the values for concrete numbers:

Occ_sum_i=700, Occ_x_i=800==>Rank_i=535.9
Occ_sum_i=70, Occ_x_i=80==>Rank_i=53.6
Occ_sum_i=4000, Occ_x_i=8000==>Rank_i=1000
Occ_sum_i=7, Occ_x_i=8==>Rank_i=5.4
Occ_sum_i=400, Occ_x_i=800==>Rank_i=100
Occ_sum_i=70, Occ_x_i=800==>Rank_i=5.4
Occ_sum_i=7, Occ_x_i=80==>Rank_i=0.5

Other appropriate formulas can be used in a similar way.

Criterion (3) comprised in optional step 308 provides a further refinement of the base algorithm or anyone of the refinements elucidated above. Ranking of candidates may be done by considering multiple independent occurrences of N-tuples [Y1_i|Y2_i| . . . |Ym_i] and takes advantage of multiple independent occurrences. This is achieved by doing at least one of the following:

(a) Using an occurrence count of multiple occurrences as ranking value. This is preferably done when criteria (1) and/or (2) are not applied.

(b) Merge multiple occurrences of candidate pairs, computing the new merged ranks by adding the unmerged rank. This is preferably done if at least one of criteria (1) and (2) are applied.

(c) Allow permutations of the middle substrings Y1_i; Y2_i and merge multiple occurrences of candidate pairs, computing the new merged ranks by adding the unmerged rank.

Candidates may be ranked with the highest rank being the most significant result.

In next optional step 310, a refinement of the base algorithm or anyone of the refinement steps 306 and 308 may be performed by filtering a result of one or more N-tuples [Y1_i|Y2_i| . . . |Ym_i] found as candidates for representing related concepts considering specific types of a desired result. The analysis may be focused on specific results the user may want to find.

For filtering, at least one of the following may be performed.

(1) Using a minimum length for middle substrings Y1_i, Y2_i, . . . , Ym_i. This filter makes sure that candidate pairs where the empty substring is one of the siblings is the empty string is excluded from the output.

(2) Using a maximum length for the middle substrings Y1_i, Y2_i, . . . , Ym_i. This filter makes sure that related concepts found by the algorithm are within a certain length. The result is compact.

(3) Using a minimum length for at least one of the prefix and suffix string $X\_i$, $Z\_i$. This filter makes sure that related concepts found do share a left-hand-side (prefix) and/or a right-hand-side (suffix) context.

(4) Requesting that the prefix string $X\_i$ ends with a particular regular expression. For example, X may be forced to end (not to end) with a blank, to suppress (enforce) discovery of different word endings for the same word stem. For example, the following candidate pair would be suppressed (enforced) in this case: X="order," Z="the goods," Y1="ed," Y2="ing."

(5) Requesting that the suffix string $Z\_i$ starts with a particular regular expression. For example, Z may force the start with a blank.

(6) Requesting that at least one of the middle strings Y1_i, Y2_i, . . . , Ym_i has a certain value V. This filter allows to find conceptual synonyms for V.

In optional refinement step 312 generalizations and/or specializations in concepts may be found. This may be achieved by comparing at least two occurrence counts Occ_1, Occ_2, . . . , Occ_m if two or more of the middle strings Y1_i, Y2_i, . . . , Ym_i and/or if two or more concatenations of prefix and middle strings X_i+Y1_i; X_i+Y2_i; . . . ; X_i+Ym_i are explicit members of the reference set SET_r. By way of example, if the occurrence count, e.g. Occ_4, of a first respective middle string, e.g. Y4_i, is significantly greater than the occurrence count Occ_1, Occ_2, . . . , Occ_m of another middle string Y1_i, Y2_i, . . . , Ym_i being compared, the respective first middle string, e.g. Y4_i, may reasonably be considered being a more generalized concept than the other middle string Y1_i, Y2_i, . . . , Ym_i.

Figure 4B:
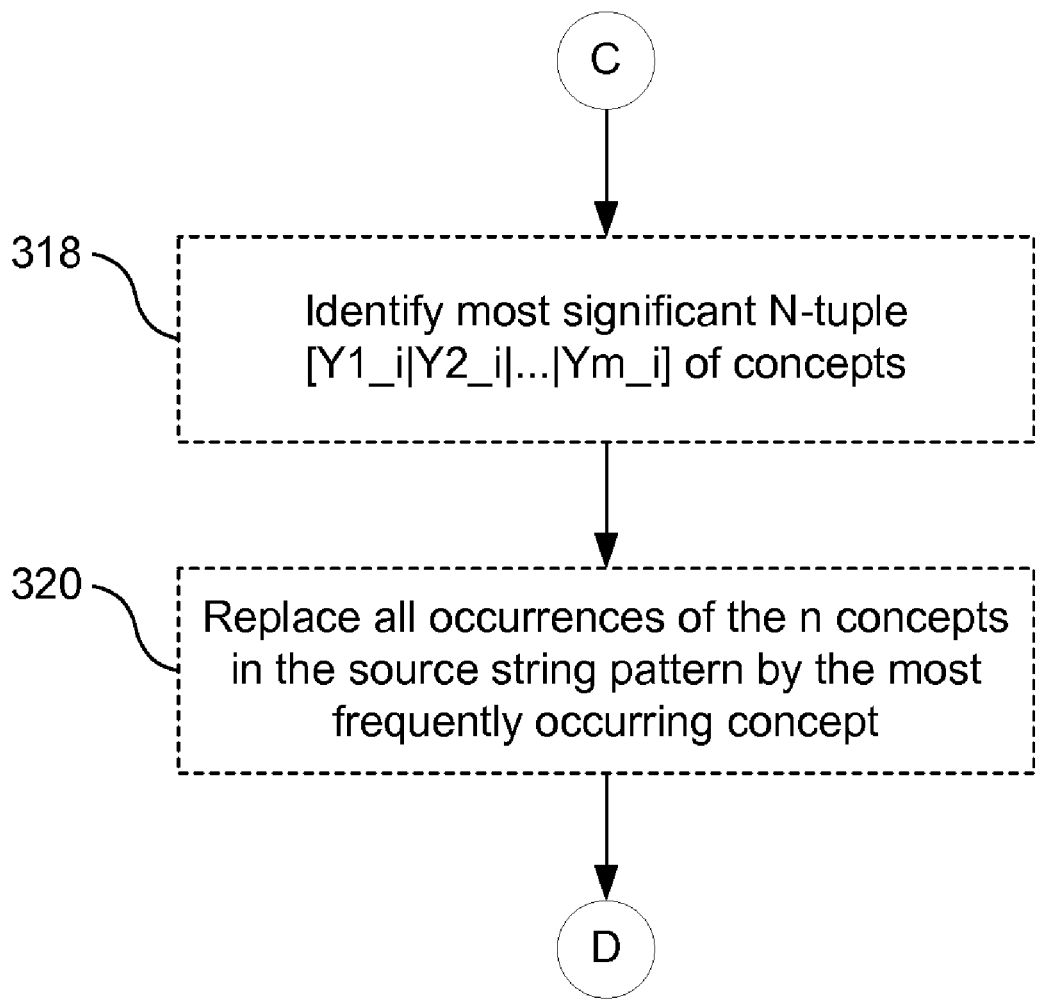

In decision step 314, it may be decided if another iteration shall be performed. If another iteration shall be performed (YES, step 314), iteration index "i" is set to i=i+1 and steps 302 to 314 are repeated. If another iteration shall not be performed (NO, step 314), then the process terminates at step 316. A further refinement of the method depicted in FIG. 4B, as shown in steps 318 and 320, may be performed as a refinement of either of the previous refinement and base algorithm steps 302 through 304 by iteratively calling algorithm.

The method as described so far may be run to identify the most significant N-tuple [Y1_i|Y2_i| . . . |Ym_i] of concepts. Here, one or more occurrences of the N concepts in the string pattern are replaced by the most frequent occurring concept yielding an altered string pattern. For example, a copy of a source text is made and all occurrences of the N-tuples [Y1_i|Y2_i| . . . |Ym_i] are replaced by the most frequently occurring concept. Then the algorithm is rerun on that copy of the source text, i.e. doing the steps in the altered string pattern as elucidated in FIG. 3A.

According to an embodiment of the invention, a program product comprising a computer useable medium including a computer readable program is proposed, wherein the computer readable program, when executed on a computer, causes the computer to perform one or "i" times the following:

(1) setting a reference set SET_r_i of strings STR_n_i;

(2) inside the reference set SET_r_i, finding specific N-tuples [Y1_i|Y2_i| ...Ym_i] of substring triples X_i,Y1_i, Z_i; X_,Y2_i,Z_i; ... ; X_i,Ym_i,Z_i with N≧2 and m=1 ... N;

(3) considering each N-tuple [Y1_i|Y2_i| ... |Ym_i] as a candidate for representing related concepts.

In one embodiment, each string STR_n_i may be denoted with its occurrence count OCC_n_i. This may be performed when the candidates should be ranked. By way of example, some results are shown. In this exemplary embodiment, the method discovers that the following related concepts are the most significant pair of related concepts:

Y1=" " (string consisting only of the blank character)

Y2="\n" (string consisting only of the newline character)

Thereby, Y1 is always much more frequent than Y2. Then replace all newlines by blanks and then rerun the algorithm on the modified text. Other examples may be performed by running the algorithm on Business Process Choreographer BPC samples web site.

A filter may be "show only concepts surrounded by blanks" as related concepts. The three most significant pairs in the output are these:

'input' and 'output' (context: '•ClientObjectWrapper $$$=bfm.c')

'ready' and 'finished' (context: 'is in the $$$ state. </p>•')

'long-running business process,' and 'microflow,' (context: ' process is a $$$ the process output message is')

By running the above-mentioned algorithm on BPC samples web site, the filter is set to 1 to 3 characters. This yields a most significant pair in output with unbalanced occurrence count:

' ' and '\n' (blank character and newline character), wherein the blank is much more general than newline character.

Furthermore, the invention can take the form of a computer program product accessible from a computer-usable or computer readable medium providing program code for use by or in connection with a computer or any instruction execution system. For the purposes of this description, a computer-usable or computer readable medium may be any apparatus that can contain, store, communicate, propagate, or transport the program for use by or in connection with the instruction execution system, apparatus, or device.

The medium may be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include compact disk-read-only memory (CD-ROM), compact disk-read/write (CD-R/W) and DVD.

Figure 5:
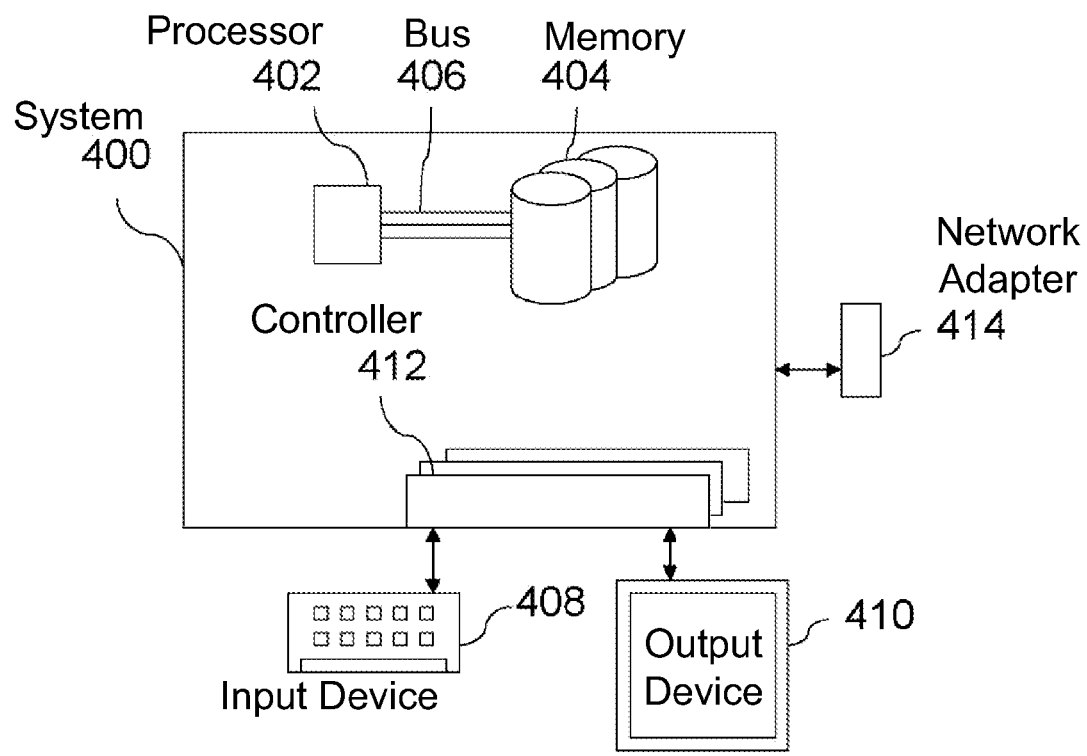
FIG. 5 is a data processing system for performing the method of FIG. 3 according to an embodiment of the present exemplary system and method.

An embodiment of a data processing system (400) (computer), as depicted in FIG. 5, suitable for storing and/or executing program code may include at least one processor (402) coupled directly or indirectly to memory elements (404) through a system bus (406). The memory elements (404) may include local memory employed during actual execution of the program code, bulk storage, and cache memories which provide temporary storage of at least some program code in order to reduce the number of times code must be retrieved from bulk storage during execution.

Input/output or I/O-devices (408, 410) (including, but not limited to keyboards, displays, pointing devices, etc.) may be coupled to the system (400) either directly or through intervening I/O controllers (412).

Network adapters (414) may also be coupled to the system (400) to enable the data processing system or remote printers or storage devices through intervening private or public networks. Modems, cable modem and Ethernet cards are just a few of the currently available types of network adapters.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims.

What is claimed is:

1. A method of analyzing a string-pattern, comprising:
defining a minimum length (Lmin_1) of substrings (STR_A_B) to be considered;
defining a maximum length (Lmax_1) of substrings (STR_A_B) to be considered;
with a computer, searching said string-pattern for substrings (STR_A_B) with a length in an interval between said minimum length (Lmin_1) and said maximum length (Lmax_1);
counting an occurrence (Occ_A_B) of each substring (STR_A_B) found with a length in the interval between said minimum length (Lmin_1) and said maximum length (Lmax_1); and
pruning away a number of said substrings (STR_A_B) that meet three criteria,
wherein said three criteria comprise (1) being contained inside a maximum substring (STR_A_C) in a subset (SET_A) of substrings (STR_A_B), (2) being shorter than said maximum substring (STR_A_C), and (3) occurring with a same frequency as said maximum substring (STR_A_C).

2. The method of claim 1, further comprising:
defining a minimum occurrence threshold for a minimum number of occurrences of said substrings (STR_A_B) contained in said string-pattern; and
pruning away said substrings (STR_A_B) with an occurrence count (Occ_A_B) less than said minimum occurrence threshold.

3. The method of claim 1, further comprising determining if said substrings found have said maximum length (Lmax_1),
wherein, if a number of said substrings (STR_A_B) have said maximum length (Lmax_1), defining a new minimum length and a new maximum length, and performing a new iteration.

4. The method of claim 3, wherein said new iteration is performed wherein said minimum length (Lmin_1) of substrings (STR_A_B) is redefined as Lmin_(A+1)=(Lmax_A)+1 and said maximum length (Lmax_1) of substrings (STR_A_B) is redefined as Lmax_(A+1)=(Lmax_A)* 2, where A is an index indicating iterations.

5. The method of claim 1, wherein said method is performed for a genome pattern.

6. The method of claim 1, wherein said method is performed for a number of iterations.

7. The method of claim 1, further comprising reducing said maximum length (Lmax_1) if a frequency of a substring (STR_A_B) found in data drops below a predetermined threshold.

8. A data processing system comprising:
a number of processors; a number of memory devices coupled to said processors; and
a display configured to display data to said user based on instructions from said processors;
wherein said processors are configured to define a threshold for a minimum number of occurrences of a number of substrings (STR_A_B) contained in a string-pattern, define a minimum length (Lmin_1) of said substrings (STR_A_B) to be considered, define a maximum length (Lmax_1) of said substrings (STR_A_B) to be considered, search said string-pattern for substrings (STR_A_B) with a length in an interval between said minimum length (Lmin_1) and said maximum length (Lmax_1), count an occurrence Occ_A_B of each substring (STR_A_B) found with lengths in the interval between said minimum length (Lmin_1) and said maximum length (Lmax_1), and prune away a number of said substrings (STR_A_B) that meets a number of criteria,
wherein said criteria are selected from the group consisting of (1) being contained inside a maximum substring (STR_A_C) in a subset (SET_A) of substrings (STR_A_B), (2) being shorter than said maximum substring (STR_A_C), (3) occurring with a same frequency as said maximum substring (STR_A_C), and combinations thereof;
wherein said number of processors is further configured to determine if said substrings found have said maximum length (Lmax_1),
wherein, if a number of said substrings (STR_A_B) has said maximum length (Lmax_1), defining new minimum and maximum lengths, and performing a new iteration.

9. The data processing system of claim 8, wherein said processor is further configured to prune away said substrings (STR_A_B) with an occurrence count (Occ_A_B) less than said minimum occurrence threshold.

10. The data processing system of claim 8, wherein said processor is further configured to perform said new iteration wherein said minimum length (Lmin_1) of substrings (STR_A_B) is redefined as Lmin_(A+1)=(Lmax_A)+1, and said maximum length (Lmax_1) of substrings (STR_A_B) is redefined as Lmax_(A+1)=(Lmax_A)*2, where A is an index indicating iterations.

11. The data processing system of claim 8, wherein said string-pattern comprises gene sequences.

12. The data processing system of claim 8, wherein searching said string-pattern for substrings (STR_A_B) with a length in an interval between said minimum length (Lmin_1) and said maximum length (Lmax_1), counting an occurrence Occ_A_B of each substring (STR_A_B) found with lengths in the interval between said minimum length (Lmin_1) and said maximum length (Lmax_1), and pruning away a number of said substrings (STR_A_B) that meets said number of criteria, are performed for a number of iterations.

13. A computer program product for analyzing a number of string-patterns, the computer program product comprising:
a computer usable storage medium having computer usable program code embodied therewith, the computer usable program code comprising:
computer usable program code configured to define a minimum length (Lmin_1) of substrings (STR_A_B) to be considered;
computer usable program code configured to define a maximum length (Lmax_1) of substrings (STR_A_B) to be considered;
computer usable program code configured to search said string-pattern for substrings (STR_A_B) with a length in an interval between said minimum length (Lmin_1) and said maximum length (Lmax_1);
computer usable program code configured to count an occurrence Occ_A_B of each substring (STR_A_B) found with lengths in the interval between said minimum length (Lmin_1) and said maximum length (Lmax_1);
computer usable program code configured to prune away a number of said substrings (STR_A_B) that meets a number of criteria,
wherein said criteria are selected from the group consisting of (1) being contained inside a maximum substring (STR_A_C) in a subset (SET_A) of substrings (STR_A_B), (2) being shorter than said maximum substring (STR_A_C), (3) occurring with a same frequency as said maximum substring (STR_A_C), and combinations thereof, computer usable program code configured to determine if said substrings found has said maximum length (Lmax_1), wherein, if a number of said substrings (STR_A_B) has said maximum length (Lmax_1), defining new minimum and maximum lengths, and performing a new iteration; and computer usable program code configured to perform said new iteration wherein said minimum length (Lmin_1) of substrings (STR_A_B) is redefined as Lmin_(A+1)=(Lmax_A)+1, and said maximum length (Lmax_1) of substrings (STR_A_B) is redefined as Lmax_(A+1)=(Lmax_A)*2, where A is an index indicating iterations.

14. The computer program product of claim 13, further comprising:

computer usable program code configured to define a threshold for a minimum number of occurrences of a number of substrings (STR_A_B) contained in said string-pattern; and computer usable program code configured to prune away said substrings (STR_A_B) with an occurrence count (Occ_A_B) less than said minimum occurrence threshold.

15. The computer program product of claim 13, further comprising computer usable program code configured to search said string-pattern for substrings (STR_A_B) with a length in an interval between said minimum length (Lmin_1) and said maximum length (Lmax_1), count an occurrence Occ_A_B of each substring (STR_A_B) found with lengths in the interval between said minimum length (Lmin_1) and said maximum length (Lmax_1), and prune away a number of said substrings (STR_A_B) that meets a number of criteria, for a number of iterations.

16. The method of claim 13, further comprising ending iteration when Lmax_A exceeds a predetermined length.

* * * * *